(12) United States Patent
Aono et al.

(10) Patent No.: US 10,951,800 B2
(45) Date of Patent: Mar. 16, 2021

(54) ENDOSCOPE SYSTEM AND ENDOSCOPE PROCESSOR

(71) Applicant: OLYMPUS CORPORATION, Tokyo (JP)

(72) Inventors: Susumu Aono, Hachioji (JP); Toshiaki Watanabe, Hino (JP); Satoshi Takekoshi, Hachioji (JP); Masakazu Mizoguchi, Hachioji (JP); Junichi Tashiro, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/906,641

(22) Filed: Jun. 19, 2020

(65) Prior Publication Data
US 2020/0322512 A1    Oct. 8, 2020

Related U.S. Application Data

(63) Continuation of application No. PCT/JP2018/039677, filed on Oct. 25, 2018.

(30) Foreign Application Priority Data

Dec. 19, 2017 (JP) .............................. JP2017-242985

(51) Int. Cl.
*H04N 5/225* (2006.01)
*A61B 1/04* (2006.01)
(Continued)

(52) U.S. Cl.
CPC ........... *H04N 5/2256* (2013.01); *A61B 1/043* (2013.01); *A61B 1/045* (2013.01); *H04N 5/76* (2013.01); *H04N 2005/2255* (2013.01)

(58) Field of Classification Search
None
See application file for complete search history.

(56) References Cited

U.S. PATENT DOCUMENTS

2003/0169247 A1* 9/2003 Kawabe ............... G09G 3/3648
345/204
2010/0049058 A1  2/2010 Ishihara
(Continued)

FOREIGN PATENT DOCUMENTS

EP     3037030 A1    6/2016
JP     2001299676 A  10/2001
(Continued)

OTHER PUBLICATIONS

International Search Report dated Jan. 15, 2019 Received in International Application No. PCT/JP2018/039677, 2 Pages.

*Primary Examiner* — Eileen M Adams
(74) *Attorney, Agent, or Firm* — Scully, Scott, Murphy & Presser, P.C.

(57) ABSTRACT

An endoscope system is provided with: a processor; a light source; and an image pickup device. The processor performs control for causing reflected light images corresponding to a predetermined period before start of the fluorescence occurrence period during the fluorescence non-occurrence period, among the reflected light images, to be recorded to the first storage medium; and, furthermore, performs control for causing the reflected light images to be recorded to the first storage medium during an after-end-of-fluorescence-occurrence period corresponding to a predetermined period with an end of the fluorescence occurrence period as a start point, and performs control for causing the reflected light images not to be recorded to the first storage medium during the fluorescence non-occurrence period after an end of the after-end-of-fluorescence-occurrence period.

9 Claims, 6 Drawing Sheets

(51) Int. Cl.
*A61B 1/045* (2006.01)
*H04N 5/76* (2006.01)

(56) References Cited

U.S. PATENT DOCUMENTS

| 2014/0049626 | A1 | 2/2014 | Ishihara |
| 2015/0025391 | A1* | 1/2015 | Mackie ............ G01N 21/6428 |
| | | | 600/476 |
| 2016/0157722 | A1 | 6/2016 | Kubo et al. |
| 2017/0084024 | A1* | 3/2017 | Gurevich ............ A61B 5/4842 |

FOREIGN PATENT DOCUMENTS

| JP | 2002119463 A | 4/2002 |
| JP | 2008154846 A | 7/2006 |
| WO | 2008078742 A1 | 7/2008 |
| WO | 2012147820 A1 | 11/2012 |
| WO | 2015025640 A1 | 2/2015 |

* cited by examiner

ENDOSCOPE SYSTEM AND ENDOSCOPE PROCESSOR

CROSS REFERENCE TO RELATED APPLICATION

This application is a continuation application of PCT/JP2018/039677 filed on Oct. 25, 2018 and claims benefit of Japanese Application No. 2017-242985 filed in Japan on Dec. 19, 2017, the entire contents of which are incorporated herein by this reference.

BACKGROUND OF THE INVENTION

1. Field of the Invention

The present invention relates to an endoscope system and an endoscope processor, and in particular to an endoscope system used for observation of an inside of a subject and an endoscope processor.

2. Description of the Related Art

In endoscopic observation in a medical field, white light observation has been conventionally performed, which is such an observation method that, by radiating red light, green light and blue light by time division or simultaneously, for example, to an object such as living tissue existing inside a subject, white light images provided with visibility that is substantially the same as visibility in the case of seeing the subject with naked eyes are acquired.

Further, in endoscopic observation in the medical field, special light observation has been conventionally performed, which is such an observation method that, by radiating special light, for example, to living tissue existing inside a subject, the special light being light to which bandwidth restrictions are applied according to characteristics of a predetermined target object included in the living tissue, special light images in which visibility of the predetermined target object is improved in comparison with the white light observation are acquired.

As the special light observation described above, fluorescence observation has been conventionally known, which is such an observation method that, by radiating, for example, to living tissue existing inside a subject to whom an fluorescent agent has been administered in advance, excitation light including an excitation wavelength of the fluorescent agent and picking up images of fluorescence emitted from the living tissue in response to the radiation of the excitation light, fluorescence images with improved visibility of a lesion or the like in the living tissue are acquired.

More specifically, for example, Japanese Patent Application Laid-Open Publication No. 2001-299676 discloses such a configuration that, by radiating excitation light with a wavelength of 790 nm to a living-body observation part into which ICG (indocyanine green) has been injected in advance, and picking up images of fluorescence emitted from the living-body observation part in response to the radiation of the excitation light, fluorescence images with improved visibility of a sentinel lymph node included in the living-body observation part are acquired.

SUMMARY OF THE INVENTION

An endoscope system of an aspect of the present invention is provided with: a processor; a light source configured to be capable of emitting excitation light for causing a fluorescent agent administered to a subject to be excited and illumination light for illuminating an inside of the subject; and an image pickup device configured to pick up images of each of fluorescence that occurs in response to radiation of the excitation light to an object existing inside the subject to whom the fluorescent agent has been administered, and reflected light that occurs in response to radiation of the illumination light to the object; wherein the processor generates and sequentially outputs reflected light images which are images corresponding to the reflected light picked up by the image pickup device; generates and sequentially outputs fluorescence images which are images corresponding to the fluorescence light picked up by the image pickup device; records each of the sequentially outputted reflected light images and the sequentially outputted fluorescence images to a first storage medium; performs control for causing the reflected light images and the fluorescence images to be recorded to the first storage medium in a fluorescence occurrence period, which is a period during which the fluorescence occurs, performs control for causing the fluorescence images not to be recorded to the first storage medium during a fluorescence non-occurrence period, which is a period during which the fluorescence does not occur, and performs control for causing reflected light images corresponding to a predetermined period before start of the fluorescence occurrence period during the fluorescence non-occurrence period, among the reflected light images, to be recorded to the first storage medium; and furthermore, performs control for causing the reflected light images to be recorded to the first storage medium during an after-end-of-fluorescence-occurrence period corresponding to a predetermined period with an end of the fluorescence occurrence period as a start point, and performs control for causing the reflected light images not to be recorded to the first storage medium during the fluorescence non-occurrence period after an end of the after-end-of-fluorescence-occurrence period.

An endoscope system of another aspect of the present invention is provided with: a processor; a light source configured to be capable of emitting excitation light for causing a fluorescent agent administered to a subject to be excited and illumination light for illuminating an inside of the subject; and an image pickup device configured to pick up images of each of fluorescence that occurs in response to radiation of the excitation light to an object existing inside the subject to whom the fluorescent agent has been administered, and reflected light that occurs in response to radiation of the illumination light to the object; wherein the processor generates and sequentially outputs reflected light images which are images corresponding to the reflected light picked up by the image pickup device; generates and sequentially outputs fluorescence images which are images corresponding to the fluorescence light picked up by the image pickup device; records each of the sequentially outputted reflected light images and the sequentially outputted fluorescence images to a first storage medium; performs control for causing the reflected light images and the fluorescence images to be recorded to the first storage medium in a fluorescence occurrence period, which is a period during which the fluorescence occurs, performs control for causing the fluorescence images not to be recorded to the first storage medium in a fluorescence non-occurrence period, which is a period during which the fluorescence does not occur, and performs control for causing the reflected light images corresponding to a predetermined period before start of the fluorescence occurrence period during the fluorescence non-occurrence period, among the reflected light images, to be recorded to the first storage medium; furthermore, holds a predetermined number of the sequentially outputted reflected light images in a second storage medium; and performs control for causing the predetermined number of the reflected light images to be held in the second storage medium during a before-start-of-fluorescence-occurrence period corresponding to a period before start of occurrence of the fluorescence during the fluorescence non-occurrence period, and performs control for causing output of the reflected light images to the second storage medium to be stopped, control for causing the predetermined number of the reflected light images held in the second storage medium to be outputted to the first storage medium and control for causing recording of the sequentially outputted reflected light images to the first storage medium to be started, at the start of the fluorescence occurrence period.

An endoscope processor of an aspect of the present invention includes a processor configured to process a signal about fluorescence generated by causing a fluorescent agent administered to a subject to be excited and a signal about reflected light that occurs in response to illumination to an inside of the subject; wherein the processor generates reflected light images from the signal about the reflected light and sequentially outputs the reflected light images; generates fluorescence images from the signal about the fluorescence and sequentially outputs the fluorescence light images; performs control for causing the reflected light images and the fluorescence images to be recorded to an external recording apparatus in a fluorescence occurrence period, which is a period during which the fluorescence occurs, performs control for causing the fluorescence images not to be recorded to the external recording apparatus in a fluorescence non-occurrence period, which is a period during which the fluorescence does not occur, and performs control for causing reflected light images corresponding to a predetermined period before start of the fluorescence occurrence period during the fluorescence non-occurrence period, among the reflected light images, to be recorded to the external recording apparatus; and furthermore, performs control for causing the reflected light images to be recorded to the external recording apparatus during an after-end-of-fluorescence-occurrence period corresponding to a predetermined period with an end of the fluorescence occurrence period as a start point, and performs control for causing the reflected light images not to be recorded to the external recording apparatus during the fluorescence non-occurrence period after an end of the after-end-of-fluorescence-occurrence period.

DETAILED DESCRIPTION OF THE PREFERRED EMBODIMENT(S)

An embodiment of the present invention will be described below with reference to drawings.

FIGS. 1 to 9 relate to the embodiment of the present invention.

Figure 1:
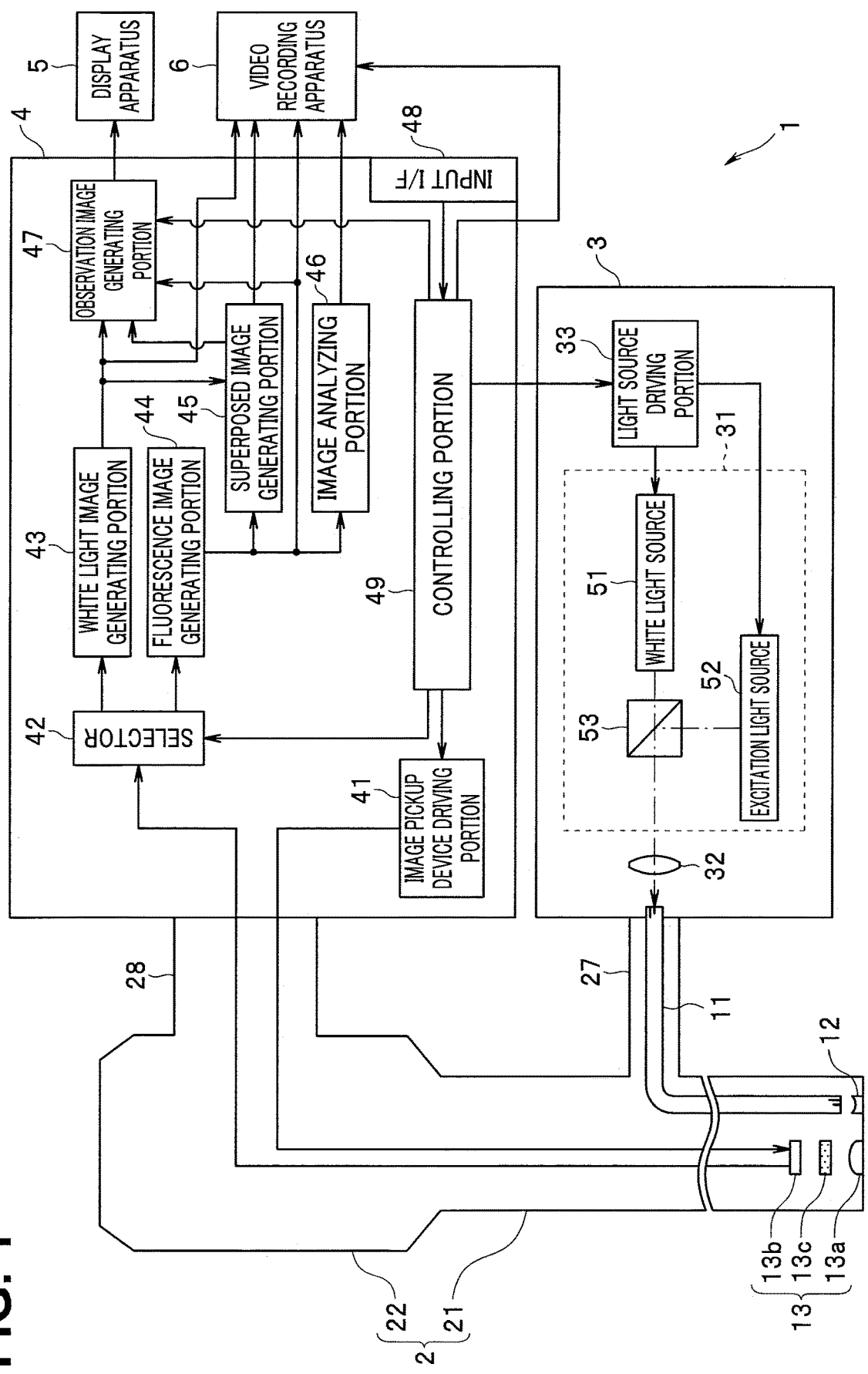
FIG. 1 is a diagram showing a configuration of a main part of an endoscope system according to an embodiment.

For example, as shown in FIG. 1, an endoscope system 1 has an endoscope 2 which is to be inserted into an inside of a subject and is configured to pick up images of an object such as living tissue existing inside the subject and output an image pickup signal, a light source apparatus 3 configured to supply light to be radiated to the object, to the endoscope 2, a processor 4 configured to, by performing various processing for the image pickup signal outputted from the endoscope 2, generate and output an observation image; a display apparatus 5 configured to display the observation image outputted from the processor 4 on a screen; and a video recording apparatus 6 configured to video-record the image outputted from the processor 4. FIG. 1 is a diagram showing a configuration of a main part of an endoscope system according to the embodiment.

For example, as shown in FIG. 1, the endoscope 2 is configured having an insertion portion 21 formed in an elongated shape insertable into an inside of a subject and an operation portion 22 provided on a proximal end side of the insertion portion 21. The endoscope 2 is provided with a configuration of being attachable to and detachable from the light source apparatus 3 via a light guide cable 27. Further, the endoscope 2 is provided with a configuration of being attachable to and detachable from the processor 4 via a signal cable 28 extended from the operation portion 22.

A light guide 11 for transmitting light supplied from the light source apparatus 3 is inserted inside the insertion portion 21 and the light guide cable 27.

As shown in FIG. 1, an emission end portion of the light guide 11 is arranged near an illumination lens 12 on a distal end portion of the insertion portion 21. As shown in FIG. 1, an incident end portion of the light guide 11 is arranged near a condensing lens 32 in the light source apparatus 3 connected to the endoscope 2 via the light guide cable 27.

On the distal end portion of the insertion portion 21, the illumination lens 12 for emitting light transmitted by the light guide 11 to an object and an image pickup portion 13 for picking up images of return light from the object are provided.

The image pickup portion 13 is configured to pick up images of each of fluorescence FLA (to be described later) that occurs in response to radiation of excitation light EXA (to be described later) to an object existing inside a subject to whom fluorescent agent has been administered, and reflected light that occurs in response to radiation of white light WLA (to be described later) to the object. The image pickup portion 13 has an objective lens 13a configured to receive return light from the object, an image pickup device 13b configured to pick up images of the return light, and an excitation light cut filter 13c arranged on an optical path from the objective lens 13a to the image pickup device 13b.

The image pickup device 13b is provided, for example, with a color CMOS image sensor, and is configured to perform an image pickup operation corresponding to an image pickup device driving signal outputted from the processor 4. Further, the image pickup device 13b is configured to pick up images of light transmitted through the excitation light cut filter 13c to generate an image pickup signal and output the generated image pickup signal to the processor 4.

The excitation light cut filter 13c is formed being provided with such an optical characteristic that cuts off, for example, the same wavelength band as the excitation light EXA among respective wavelength bands included in light emitted through the objective lens 13a, and causes wavelength bands different from a wavelength band of the excitation light EXA to be transmitted. In other words, the excitation light cut filter 13c is formed being provided with such an optical characteristic that causes the fluorescence FLA and the white light WLA emitted from a fluorescent agent in response to radiation of the excitation light EXA to be transmitted.

The operation portion 22 is provided on the proximal end side of the insertion portion 21 and is formed being provided with a shape that can be grasped by a user such as a surgeon. Further, the operation portion 22 is provided, for example, with a scope switch (not shown) which is one or more switches capable of giving various instructions corresponding to operations by the user to the processor 4.

For example, as shown in FIG. 1, the light source apparatus 3 is configured having a light emitting portion 31, the condensing lens 32 and a light source driving portion 33.

The light emitting portion 31 is configured having a white light source 51, an excitation light source 52 and a dichroic mirror 53.

The white light source 51 is configured being provided, for example, with any of a xenon lamp, a white light LED, and an RGB three-color LED. The white light source 51 is configured to generate, for example, the white light WLA, which is light including respective wavelength bands of a red region, a green region and a blue region, in response to a light source driving signal outputted from the light source driving portion 33. Note that, in the present embodiment, the light source apparatus 3 may be provided, for example, with a broadband light source configured being provided with a lamp that emits broadband light, which is light provided with a wavelength band at least from the blue region to a near-infrared region, and an optical filter provided with such an optical characteristic that causes the same wavelength band as the white light WLA, among respective wavelength bands included in the broadband light, to be transmitted and cuts out other wavelength bands, instead of the white light source 51.

The excitation light source 52 is configured, for example, being provided with an LD (a laser diode). Further, the excitation light source 52 is configured to generate, for example, the excitation light EXA, which is narrowband light including an excitation wavelength of a predetermined fluorescent agent administered to a subject, in response to a light source driving signal outputted from the light source driving portion 33. Note that, hereinafter, description will be made on an assumption that the fluorescent agent administered to a subject is ICG (indocyanine green), that the excitation light EXA is narrowband near-infrared light including an excitation wavelength of the ICG (for example, a wavelength of 808 nm or a near 808 nm), and that the fluorescence FLA, which is near-infrared light belonging to a wavelength band on a longer wavelength side than the excitation light EXA, is emitted from the ICG, unless otherwise stated.

The dichroic mirror 53 is configured being provided, for example, with such an optical characteristic that causes the white light WLA emitted from the white light source 51 to be transmitted to emit the white light WLA to the condensing lens 32 side, and reflects the excitation light EXA emitted from the excitation light source 52 to emit the excitation light EXA to the condensing lens 32 side.

In other words, the light emitting portion 31 is configured to be capable of generating the white light WLA by causing the white light source 51 to emit light in response to a driving signal outputted from the light source driving portion 33. Further, the light emitting portion 31 is configured to be capable of generating the excitation light EXA by causing the excitation light source 52 to emit light in response to a driving signal outputted from the light source driving portion 33. Further, the light emitting portion 31 is configured to be capable of emitting the white light WLA and the excitation light EXA to the condensing lens 32.

The condensing lens 32 is configured to condense light emitted from the light emitting portion 31 and emit the light to the incident end portion of the light guide 11.

The light source driving portion 33 is configured to generate a light source driving signal for driving the white light source 51 and the excitation light source 52 to output the light source driving signal to the light emitting portion 31, based on a control signal outputted from the processor 4.

In other words, the light source apparatus 3 is configured to be capable of emitting the excitation light EXA for causing a fluorescent agent administered to a subject to be excited and the white light WLA which is illumination light for illuminating an inside of the subject.

For example, as shown in FIG. 1, the processor 4 is configured having an image pickup device driving portion 41, a selector 42, a white light image generating portion 43, a fluorescence image generating portion 44, a superposed image generating portion 45, an image analyzing portion 46, an observation image generating portion 47, an input I/F (interface) 48 and a controlling portion 49. Note that, in the present embodiment, each of portions other than the input I/F 48 in the processor 4 may be configured as an individual electronic circuit or may be configured as a circuit block in an integrated circuit such as an FPGA (field programmable gate array). Further, in the present embodiment, for example, the processor 4 may be configured being provided with one or more CPUs. Further, by appropriately modifying a configuration according to the present embodiment, for example, a program for causing a function of each of the portions other than the input I/F 48 in the processor 4 to be executed may be read from a storage medium such as a memory, and an operation according to the read program may be performed on a computer.

The image pickup device driving portion 41 is configured to generate and output an image pickup device driving signal for causing the image pickup device 13b to be driven, based on a control signal outputted from the controlling portion 49.

The selector 42 is configured to perform an operation for setting an output destination of an image pickup signal outputted from the endoscope 2 to either the white light image generating portion 43 or the fluorescence image generating portion 44, based on a control signal outputted from the controlling portion 49.

The white light image generating portion 43 is configured to generate white light images WIA based on an image pickup signal outputted via the selector 42 and sequentially output the generated white light images WIA to each of the superposed image generating portion 45, the observation image generating portion 47 and the video recording apparatus 6 one by one. In other words, the white light image generating portion 43 is provided with a function as a reflected light image generating portion and is configured to generate the white light images WIA which are images corresponding to reflected light of the white light WLA which have been picked up by the image pickup portion 13.

The fluorescence image generating portion 44 is configured to generate fluorescence images FIA based on an image pickup signal outputted via the selector 42 and sequentially output the generated fluorescence images FIA to each of the superposed image generating portion 45, the image analyzing portion 46, the observation image generating portion 47 and the video recording apparatus 6 one by one. In other words, the fluorescence image generating portion 44 is configured to generate the fluorescence images FIA which are images corresponding to the fluorescence FLA which have been picked up by the image pickup portion 13.

The superposed image generating portion 45 is configured to generate superposed images SIA by performing a process for superposing the white light images WIA outputted from the white light image generating portion 43 and the fluorescence images FIA outputted from the fluorescence image generating portion 44 and sequentially output the generated superposed images SIA to each of the observation image generating portion 47 and the video recording apparatus 6 one by one.

More specifically, the superposed image generating portion 45 performs such a process that, by superposing a pixel value of a pixel WP at one pixel position on a white light image WIA outputted from the white light image generating portion 43 and a pixel value of a pixel FP at the one pixel position on a fluorescence image FIA outputted from the fluorescence image generating portion 44, a pixel value of a pixel SP at the one pixel position on a superposed image SIA for the whole image area, for example, using Equation (1) below.

Note that, in Equation (1) below, it is assumed that Ri indicates a brightness value of a red component of the pixel WP, Gi indicates a brightness value of a green component of the pixel WP, Bi indicates a brightness value of a blue component of the pixel WP, Fi indicates a brightness value of (a fluorescence component) of the pixel FP, Ro indicates a brightness value of a red component of the pixel SP, Go indicates a brightness value of a green component of the pixel SP, and Bo indicates a brightness value of a blue component of the pixel SP. Further, a, β and y in Equation (1) below indicate weight coefficients for specifying a color tone at a position where the fluorescence FLA included in the superposed image SIA occurs and may be, for example, fixed values set in advance by the superposed image generating portion 45 or variable values set according to a control signal from the controlling portion 49.

$$\begin{pmatrix} Ro \\ Go \\ Bo \end{pmatrix} = \begin{pmatrix} 1 & 0 & 0 & \alpha \\ 0 & 1 & 0 & \beta \\ 0 & 0 & 1 & \gamma \end{pmatrix} \begin{pmatrix} Ri \\ Gi \\ Bi \\ Fi \end{pmatrix} \quad (1)$$

The image analyzing portion 46 is configured to perform a process for analyzing whether a fluorescence occurrence area is included in the fluorescence image FIA based on a feature value related to brightness of the fluorescence image FIA outputted from the fluorescence image generating portion 44 and output analysis result information showing an analysis result obtained by the process to the video recording apparatus 6.

More specifically, the image analyzing portion 46 performs, for example, a process for calculating a feature value FAV related to brightness of a fluorescence image FIA outputted from the fluorescence image generating portion 44 and judging whether or not the calculated feature value FAV is equal to or above a predetermined threshold THV. Then, for example, when detecting that the feature value FAV is equal to or above the threshold THV, the image analyzing portion 46 acquires an analysis result that a fluorescence occurrence area is included in the fluorescence image FIA outputted from the fluorescence image generating portion 44, and outputs analysis result information showing the acquired analysis result to the video recording apparatus 6. For example, when detecting that the feature value FAV is below the threshold THV, the image analyzing portion 46 acquires an analysis result that an fluorescence occurrence area is not included in the fluorescence image FIA outputted from the fluorescence image generating portion 44, and outputs analysis result information showing the acquired analysis result to the video recording apparatus 6.

Note that the image analyzing portion 46 of the present embodiment may be configured to perform the process, for example, using an arbitrary feature value like an average value of brightness values of respective pixels included in the fluorescence image FIA outputted from the fluorescence image generating portion 44 as the feature value FAV as far as it is possible to identify whether an fluorescence occurrence area is included in the fluorescence image FIA or not. Further, in the present embodiment, the image analyzing portion 46 may be provided in the video recording apparatus 6.

The observation image generating portion 47 is configured to generate an observation image based on a white light image WIA outputted from the white light image generating portion 43, a fluorescence image FIA outputted from the fluorescence image generating portion 44, a superposed image SIA outputted from the superposed image generating portion 45 and a control signal outputted from the controlling portion 49 and output the generated observation image to the display apparatus 5.

The input I/F (interface) 48 is configured being provided one or more switches and/or buttons capable of giving an instruction corresponding to an operation by the user. More specifically, the input I/F 48 is configured being provided, for example, with an observation mode switching switch (not shown) capable of giving an instruction for setting (switching) an observation mode of the endoscope system 1 to either a white light observation mode or a fluorescence observation mode. Further, the input I/F 48 is configured being provided, for example, with a display image switching switch (not shown) capable of giving an instruction for setting (switching) an image caused to be displayed on the display apparatus 5 in the fluorescence observation mode to either the white light image WIA or the superposed image SIA.

The controlling portion 49 is configured to be capable of generating a control signal for causing an operation corresponding to an instruction from the input I/F 48 to be performed, and output the control signal to each of the light source driving portion 33 and the observation image generating portion 47. Further, the controlling portion 49 is configured being provided with a storage medium (not shown) such as a memory in which control information to be used at the time of controlling each portion of the endoscope system 1 is stored.

The controlling portion 49 is configured to generate a control signal related to an image pickup operation to be performed by the image pickup device 13b, according to an observation mode set by the observation mode switching switch of the input I/F 48, and output the control signal to the image pickup device driving portion 41. Further, the controlling portion 49 is configured to generate a control signal for setting an output destination of an image pickup signal to be inputted to the processor 4, according to an observation mode set by the observation mode switching switch of the input I/F 48, and output the control signal to the selector 42. Further, the controlling portion 49 is configured to generate observation mode information including information by which a currently set observation mode of the endoscope system 1 can be identified, based on an instruction from the observation mode switching switch of the input I/F 48 and output the generated observation mode information to the video recording apparatus 6.

The display apparatus 5 is provided, for example, with an LCD (liquid crystal display) and the like and is configured to be capable of displaying an observation image and the like outputted from the processor 4.

Figure 2:
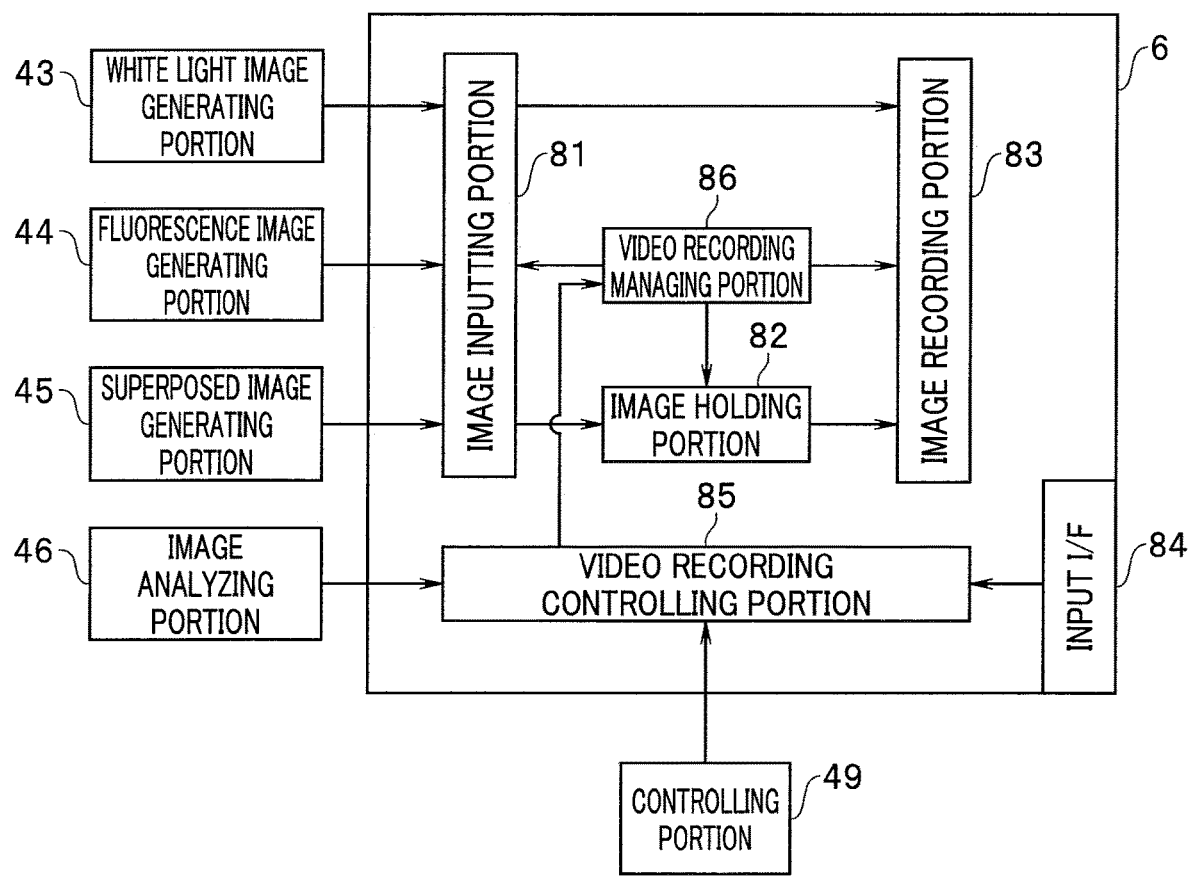
FIG. 2 is a block diagram for illustrating an example of a specific configuration of a video recording apparatus in the endoscope system according to the embodiment.

The video recording apparatus 6 is configured to perform an operation for recording, among respective images outputted from the white light image generating portion 43, the fluorescence image generating portion 44 and the superposed image generating portion 45, an image corresponding to an analysis result outputted from the image analyzing portion 46 and observation mode information outputted from the controlling portion 49. For example, as shown in FIG. 2, the video recording apparatus 6 is configured having an image inputting portion 81, an image holding portion 82, an image recording portion 83, an input I/F 84, a video recording controlling portion 85 and a video recording managing portion 86. Note that, in the present embodiment, each of portions other than the input I/F 84 in the video recording apparatus 6 may be configured as an individual electronic circuit or may be configured as a circuit block in an integrated circuit such as an FPGA (field programmable gate array). Further, in the present embodiment, for example, the video recording apparatus 6 may be configured being provided with one or more CPUs. Further, by appropriately modifying a configuration according to the present embodiment, for example, a program for causing a function of each of the portions other than the input I/F 84 in the video recording apparatus 6 to be executed may be read from a storage medium such as a memory, and an operation according to the read program may be performed on a computer. FIG. 2 is a block diagram for illustrating an example of a specific configuration of a video recording apparatus in the endoscope system according to the embodiment.

The image inputting portion 81 is configured so that each of white light images WIA sequentially outputted from the white light image generating portion 43, fluorescence images FIA sequentially outputted from the fluorescence image generating portion 44 and superposed images SIA sequentially outputted from the superposed image generating portion 45 is inputted. Further, the image inputting portion 81 is configured to perform an operation for outputting at least one image among the white light images WIA, the fluorescence images FIA and the superposed images SIA to an output destination corresponding to control of the video recording managing portion 86.

The image holding portion 82 constituting a second storage medium is configured being provided, for example, with a volatile storage medium like a video memory. Further, the image holding portion 82 is configured to be capable of holding a predetermined number of images sequentially outputted via the image inputting portion 81. In other words, the image holding portion 82 is configured to be capable of holding a predetermined number of white light images WIA sequentially outputted from the white light image generating portion 43 via the image inputting portion 81. Further, the image holding portion 82 is configured to perform an operation for replacing the oldest image among the currently held predetermined number of images with the newest image outputted via the image inputting portion 81. Further, the image holding portion 82 is configured to perform an operation for outputting the currently held predetermined number of images to the image recording portion 83 according to control of the video recording managing portion 86.

The image recording portion 83 constituting a first storage medium is configured being provided, for example, with a nonvolatile storage medium like a hard disk or the like. The image recording portion 83 is configured to be capable of recording each of the white light images WIA sequentially outputted from the white light image generating portion 43 via the image inputting portion 81, the fluorescence images FIA sequentially outputted from the fluorescence image generating portion 44 via the image inputting portion 81 and the superposed images SIA sequentially outputted from the superposed image generating portion 45 via the image inputting portion 81. Further, the image recording portion 83 is configured to perform an operation for recording at least one image among the white light images WIA, the fluorescence images FIA and the superposed images SIA according to control of the video recording managing portion 86. Further, the image recording portion 83 is configured to perform an operation for generating and recording additional information about currently recorded images, according to control of the video recording managing portion 86.

The input I/F 84 is configured being provided one or more switches and/or buttons capable of giving an instruction corresponding to an operation by the user. More specifically, the input I/F 84 is configured being provided, for example, with a recorded image setting switch (not shown) capable of giving an instruction for setting at least one image among the white light images WIA, the fluorescence images FIA and the superposed images SIA, as an image caused to be recorded to the video recording apparatus 6. Further, the input I/F 84 is configured being provided, for example, with a video recording mode setting switch (not shown) capable of giving an instruction for setting a video recording mode in the case of causing white light images WIA or superposed images SIA to be recorded to the video recording apparatus 6, to one video recording mode among a plurality of video recording modes.

The video recording controlling portion 85 is configured to generate and output video recording control information, which is information to be used for control by the video recording managing portion 86, based on analysis result information outputted from the image analyzing portion 46, observation mode information outputted from the controlling portion 49 and an instruction from the input I/F 84. Note that a specific example of the operation performed by the video recording controlling portion 85 will be described later.

The video recording managing portion 86 is configured to control an operation of each of the image inputting portion 81, the image holding portion 82 and the image recording portion 83 based on the video recording control information outputted from the video recording controlling portion 85. Note that a specific example of the control performed by the video recording managing portion 86 will be described later. Note that, in the present embodiment, for example, the video recording managing portion 86 may be provided in the processor 4.

Next, an operation and the like of the endoscope system 1 of the present embodiment will be described. Note that, hereinafter, description will be advanced on an assumption that, before fluorescence observation of a desired object existing inside a subject is performed, ICG which is a fluorescent agent is administered to the subject or the desired object in advance.

For example, by operating the observation mode switching switch of the input I/F 48 after connecting each portion of the endoscope system 1 and turning on power, the user such as a surgeon gives an instruction for setting the observation mode of the endoscope system 1 to the white light observation mode.

When detecting that the instruction for setting the observation mode of the endoscope system 1 to the white light observation mode has been given, the controlling portion 49 outputs a control signal for causing the white light WLA to be generated, to the light source driving portion 33.

When detecting that the instruction for setting the observation mode of the endoscope system 1 to the white light observation mode has been given, the controlling portion 49 outputs a control signal for causing white light images WIA to be displayed as observation images, to the observation image generating portion 47.

When detecting that the instruction for setting the observation mode of the endoscope system 1 to the white light observation mode has been given, the controlling portion 49 generates a control signal for causing a predetermined image pickup operation to be performed and outputs the control signal to the image pickup device driving portion 41; and the controlling portion 49 also generates a control signal for setting an output destination of an image pickup signal to be inputted to the processor 4, to the white light image generating portion 43, and outputs the control signal to the selector 42.

According to the control signal outputted from the controlling portion 49, the light source driving portion 33 generates a light source driving signal for causing the white light source 51 to be turned on and causing the excitation light source 52 to be turned off and outputs the light source driving signal to the light emitting portion 31, in the white light observation mode.

According to the operation as described above, in the white light observation mode, the white light WLA emitted from the white light source 51 is supplied to the endoscope 2; images of reflected light of the white light WLA, which is return light from an object illuminated by the white light WLA, are picked up by the image pickup portion 13; and white light images WIA corresponding to an image pickup signal outputted from the image pickup portion 13 are generated by the white light image generating portion 43 and displayed on the display apparatus 5 as observation images.

For example, by operating the recorded image setting switch of the input OF 84 in the state in which the observation mode of the endoscope system 1 is set to the white light observation mode, the user gives an instruction for causing the white light images WIA to be recorded to the video recording apparatus 6.

The controlling portion 49 generates observation mode information showing that the currently set observation mode of the endoscope system 1 is the white light observation mode, based on the instruction from the observation mode switching switch of the input I/F 48, and outputs the generated observation mode information to the video recording apparatus 6.

The video recording controlling portion 85 generates video recording control information for causing the white light images WIA to be recorded to the image recording portion 83, based on the observation mode information outputted from the controlling portion 49 and the instruction from the recorded image setting switch of the input I/F 84, and outputs the video recording control information to the video recording managing portion 86.

The video recording managing portion 86 performs control for setting an output destination of the white light images WIA to the image recording portion 83, to the image inputting portion 81, based on the video recording control information outputted from the video recording controlling portion 85.

According to the operation as described above, in the white light observation mode, the white light images WIA sequentially outputted from the white light image generating portion 43 are recorded to the image recording portion 83 via the image inputting portion 81.

In the state in which the observation mode of the endoscope system 1 is set to the white light observation mode, the user inserts the insertion portion 21 into an inside of an examinee while confirming the observation images displayed on the display apparatus 5, and arranges the distal end portion of the insertion portion 21 at such a position that a desired object (living tissue) inside the examinee (including, for example, an area to be a blood flow evaluation target) is included in an observation field of view of the objective lens 13a. After that, by operating the observation mode switching switch of the input I/F 48, the user gives an instruction for setting the observation mode of the endoscope system 1 to the fluorescence observation mode. Further, by operating the display image switching switch of the input I/F 48, the user gives an instruction for causing either white light images WIA or superposed images SIA to be displayed on the display apparatus 5 as main images MIA.

When detecting that the instruction for setting the observation mode of the endoscope system 1 to the fluorescence observation mode has been given, the controlling portion 49 generates a control signal for causing observation images including main images MIA and fluorescence images FIA to be generated and outputs the control signal to the observation image generating portion 47, according to an instruction from the display image switching switch of the input I/F 48.

When detecting that the instruction for setting the observation mode of the endoscope system 1 to the fluorescence observation mode has been given, the controlling portion 49 generates a control signal for causing a timing of occurrence of the white light WLA and the excitation light EXA by the light emitting portion 31, an image pickup operation by the image pickup device 13b, and an output destination of an image pickup signal to be inputted to the processor 4 to be synchronized, and outputs the control signal to each of the light source driving portion 33, the image pickup device driving portion 41 and the selector 42.

More specifically, for example, the controlling portion 49 generates a control signal for causing the image pickup device 13b to perform a rolling-shutter-method image pickup operation and outputs the control signal to the image pickup device driving portion 41. Further, for example, the controlling portion 49 generates a control signal for causing a predetermined amount of white light WLA and the predetermined amount of excitation light EXA to be generated alternately (by time division) for each blanking period, which is a period during which reading is not performed on any line of the image pickup device 13b in the rolling shutter method image pickup operation, and outputs the control signal to the light source driving portion 33. Further, for example, the controlling portion 49 generates a control signal for setting an output destination of an image pickup signal inputted to the processor 4 when the white light WLA occurs, to the white light image generating portion 43, and setting an output destination of an image pickup signal inputted to the processor 4 when the excitation light EXA occurs, to the fluorescence image generating portion 44, and outputs the control signal to the selector 42.

According to the control of the controlling portion 49 described above, for example, the white light WLA is radiated to the object during a first blanking period of the image pickup device 13b; images of reflected light of the white light WLA, which is return light from the object, are picked up by the image pickup portion 13; an image pickup signal generated by the image pickup portion 13 are outputted to the white light image generating portion 43 via the selector 42; white light images WIA generated based on the image pickup signal are sequentially outputted to each of the superposed image generating portion 45, the observation image generating portion 47 and the video recording apparatus 6 one by one.

Further, according to the control of the controlling portion 49 described above, for example, the excitation light EXA is radiated to the object during a second blanking period of the image pickup device 13b different from the first blanking period described above; images of fluorescence FLA included in return light generated from the object are picked up by the image pickup portion 13; an image pickup signal generated by the image pickup portion 13 is outputted to the fluorescence image generating portion 44 via the selector 42; and fluorescence images FIA generated based on the image pickup signal are sequentially outputted to each of the superposed image generating portion 45, the image analyzing portion 46 and the video recording apparatus 6 one by one.

For example, in a state in which the coefficients α, β and γ of Equation (1) above are set so that α=γ=0 and β=1 are satisfied, the superposed image generating portion 45 generates superposed images SIA by performing a process for superposing white light images WIA outputted from the white light image generating portion 43 and fluorescence images FIA outputted from the fluorescence image generating portion 44 and outputs the generated superposed images SIA to each of the observation image generating portion 47 and the video recording apparatus 6. In other words, according to such an operation of the superposed image generating portion 45, such superposed images SIA that a position where fluorescence FLA in the object which has been image-picked up by the endoscope 2 is shown in green are outputted to the observation image generating portion 47 and the video recording apparatus 6.

Figure 3:
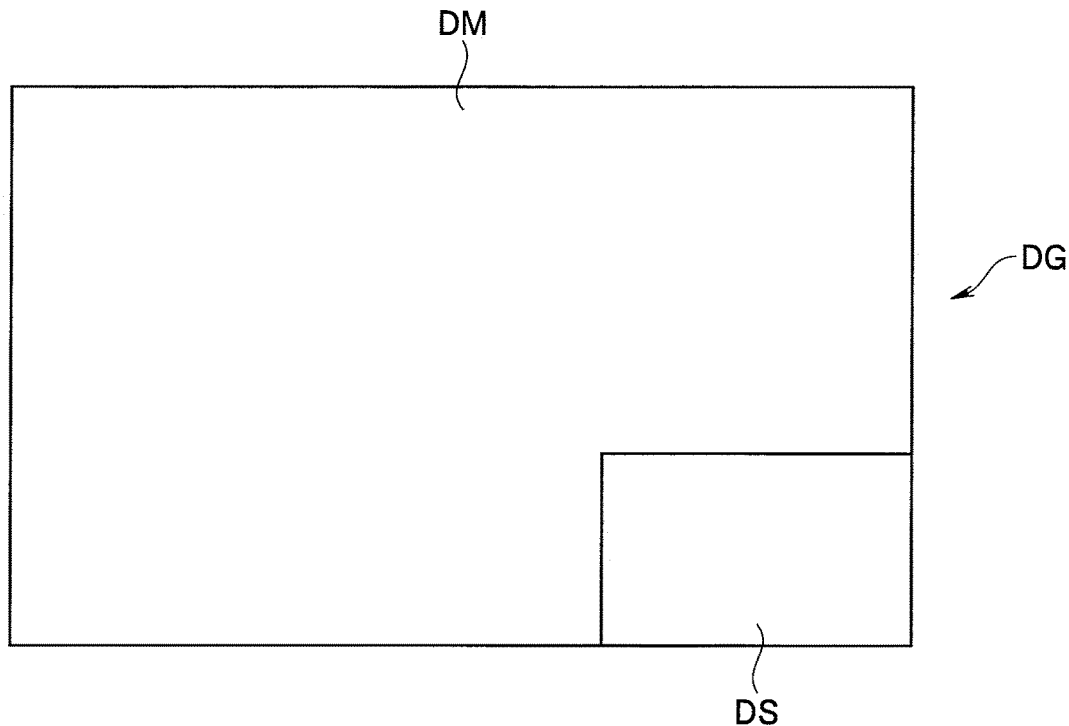
FIG. 3 is a diagram showing an example of a display aspect of an observation image displayed in a fluorescence observation mode.

According to the control signal outputted from the controlling portion 49, the observation image generating portion 47 generates, for example, such P-in-P (picture-in-picture) images that, while main images MIA are caused to be displayed in a display area DM, fluorescence images FIA are caused to be displayed in a display area DS provided on a part in the display area DM, as observation images DG, and outputs the generated observation images DG to the display apparatus 5, in the fluorescence observation mode. According to such an operation of the observation image generating portion 47, for example, the observation images DG having a display aspect as shown in FIG. 3 are displayed on the display apparatus 5. FIG. 3 is a diagram showing an example of a display aspect of an observation image displayed in the fluorescence observation mode.

For example, by operating the recorded image setting switch of the input I/F 84 in the state in which the observation mode of the endoscope system 1 is set to the fluorescence observation mode, the user gives an instruction for causing the white light images WIA and the fluorescence images FIA to be recorded to the video recording apparatus 6.

The controlling portion 49 generates observation mode information showing that the currently set observation mode of the endoscope system 1 is the fluorescence observation mode, based on the instruction of the observation mode switching switch of the input I/F 48 and outputs the generated observation mode information to the video recording apparatus 6.

The image analyzing portion 46 performs a process for analyzing whether a fluorescence occurrence area is included in the fluorescence images FIA outputted from the fluorescence image generating portion 44 and outputs analysis result information showing an analysis result obtained by the process to the video recording apparatus 6.

Here, specific examples of operations performed in a plurality of video recording modes that can be alternatively set by operating the video recording mode setting switch of the input I/F 84 will be described. Note that it is assumed that the operations performed in each video recording mode, which will be described below, are similarly applied when superposed images SIA are recorded instead of white light images WIA in the fluorescence observation mode, unless otherwise stated.

For example, by operating the video recording mode setting switch of the input I/F 84, the user gives an instruction for setting a video recording mode RMA, a video recording mode in which white light images WIA sequentially outputted from the processor 4 in the fluorescence observation mode to be continuously recorded to the video recording apparatus 6.

The video recording controlling portion 85 generates video recording control information for causing the white light images WIA to be continuously recorded to the image recording portion 83, based on the observation mode information outputted from the controlling portion 49 and the instructions from the recorded image setting switch and the video recording mode setting switch of the input I/F 84, and outputs the video recording control information to the video recording managing portion 86.

The video recording controlling portion 85 generates video recording control information for, while causing fluorescence images FIA to be recorded to the image recording portion 83 during a fluorescence occurrence period PFP, which is a period during which an analysis result that a fluorescence occurrence area is included in the fluorescence images FIA is obtained, causing fluorescence images FIA not to be recorded to the image recording portion 83 during a fluorescence non-occurrence period PFN, which is a period during which an analysis result that an fluorescence occurrence area is not included in the fluorescence images FIA is obtained, and outputs the video recording control information to the video recording managing portion 86, based on the analysis result information outputted from the image analyzing portion 46, the observation mode information outputted from the controlling portion 49 and the instruction from the recorded image setting switch of the input I/F 84.

The video recording managing portion 86 performs control for setting an output destination of the white light images WIA to the image recording portion 83, to the image inputting portion 81 based on the video recording control information outputted from the video recording controlling portion 85. Further, the video recording managing portion 86 performs control for causing output of the white light images WIA to the image recording portion 83 to be performed during the fluorescence occurrence period PFP and the fluorescence non-occurrence period PFN, to the image inputting portion 81 based on the video recording control information outputted from the video recording controlling portion 85.

The video recording managing portion 86 performs control for setting an output destination of the fluorescence images FIA to the image recording portion 83, to the image inputting portion 81 based on the video recording control information outputted from the video recording controlling portion 85. Further, the video recording managing portion 86 performs control for causing output of the fluorescence images FIA to the image recording portion 83 to be performed during the fluorescence occurrence period PFP, to the image inputting portion 81 based on the video recording control information outputted from the video recording controlling portion 85. Further, the video recording managing portion 86 performs control for causing output of the fluorescence images FIA to the image recording portion 83 to be stopped during the fluorescence non-occurrence period PFN, to the image inputting portion 81 based on the video recording control information outputted from the video recording controlling portion 85.

Figure 4:
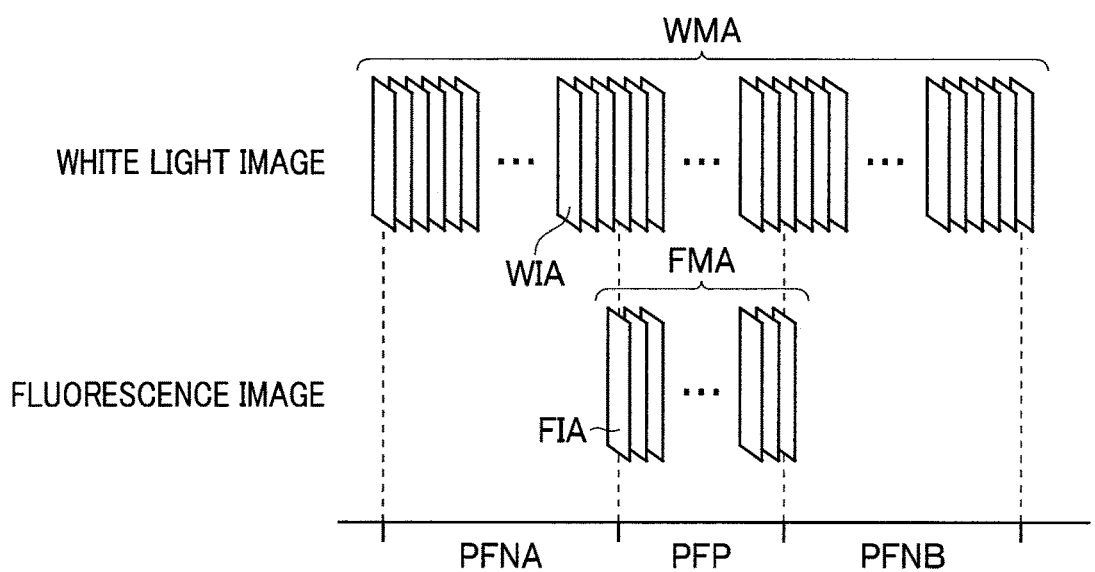
FIG. 4 is a diagram for illustrating an example of a recording state of images in the video recording apparatus according to the embodiment.

According to the operation as described above, when the video recording mode of the video recording apparatus 6 is set to the video recording mode RMA, a movie WMA corresponding to a plurality of white light images WIA sequentially inputted to the image inputting portion 81 during a before-start-of-fluorescence-occurrence period PFNA, which is a period before a start of the fluorescence occurrence period PFP during the fluorescence non-occurrence period PFN, the fluorescence occurrence period PFP, and an after-end-of-fluorescence-occurrence period PFNB, which is a period after an end of the fluorescence occurrence period PFP during the fluorescence non-occurrence period, is recorded to the image recording portion 83, for example, as shown in FIG. 4. Further, according to the operation as described above, when the video recording mode of the video recording apparatus 6 is set to the video recording mode RMA, a movie FMA corresponding to a plurality of fluorescence images FIA sequentially inputted to the image inputting portion 81 in the fluorescence occurrence period PFP is recorded to the image recording portion 83, for example, as shown in FIG. 4. FIG. 4 is a diagram for illustrating an example of a recording state of images in the video recording apparatus according to the embodiment.

In other words, when the video recording mode of the video recording apparatus 6 is set to the video recording mode RMA, the white light images WIA sequentially inputted to the video recording apparatus 6 during the before-start-of-fluorescence-occurrence period PFNA, the fluorescence occurrence period PFP and the after-end-of-fluorescence-occurrence period PFNB are recorded as the movie WMA, and the fluorescence images FIA inputted to the video recording apparatus 6 during the fluorescence occurrence period PFP are recorded as the movie FMA. Further, when the video recording mode of the video recording apparatus 6 is set to the video recording mode RMA, control for causing the white light images WIA to be recorded to the image recording portion 83 is performed by the video recording managing portion 86 during the before-start-of-fluorescence-occurrence period PFNA, the fluorescence occurrence period PFP and the after-end-of-fluorescence-occurrence period PFNB. Further, when the video recording mode of the video recording apparatus 6 is set to the video recording mode RMA, control for causing the fluorescence images FIA not to be recorded to the image recording portion 83 is performed by the video recording managing portion 86 during the fluorescence non-occurrence period PFN. Further, when the video recording mode of the video recording apparatus 6 is set to the video recording mode RMA, control for causing the fluorescence images FIA to be recorded to the image recording portion 83 is performed by the video recording managing portion 86 during the fluorescence occurrence period PFP.

Note that, in the present embodiment, for example, a timing when the video recording controlling portion 85 detects that the observation mode of the endoscope system 1 has been switched from the white light observation mode to the fluorescence observation mode may be a start point of the before-start-of-fluorescence-occurrence period PFNA. Further, in the present embodiment, for example, a timing when the video recording controlling portion 85 detects that the observation mode of the endoscope system 1 has been switched from the fluorescence observation mode to the white light observation mode may be an end point of the after-end-of-fluorescence-occurrence period PFNB.

For example, by operating the video recording mode setting switch of the input I/F 84, the user gives an instruction for setting a video recording mode RMB, a video recording mode in which white light images WIA sequentially outputted from the processor 4 in the fluorescence observation mode to be recorded to the video recording apparatus 6 during a predetermined period.

The video recording controlling portion 85 generates video recording control information for causing recording of the white light images WIA to be continued until a time point after a predetermined period after the end of the fluorescence occurrence period PFP, and outputs the video recording control information to the video recording managing portion 86, based on the analysis result information outputted from the image analyzing portion 46, the observation mode information outputted from the controlling portion 49, and the instructions from recorded image setting switch and the video recording mode setting switch of the input I/F 84. Further, the video recording controlling portion 85 generates video recording control information for, while causing fluorescence images FIA to be recorded to the image recording portion 83 during the fluorescence occurrence period PFP, causing the fluorescence images FIA not to be recorded to the image recording portion 83 during the fluorescence non-occurrence period PFN, and outputs the video recording control information to the video recording managing portion 86, based on the analysis result information outputted from the image analyzing portion 46, the observation mode information outputted from the controlling portion 49 and the instruction from the recorded image setting switch of the input I/F 84.

The video recording managing portion 86 performs control for setting an output destination of the white light images WIA to the image recording portion 83, to the image inputting portion 81 based on the video recording control information outputted from the video recording controlling portion 85. Further, the video recording managing portion 86 performs control for causing output of the white light images WIA to the image recording portion 83 to be performed during the before-start-of-fluorescence-occurrence period PFNA, the fluorescence occurrence period PFP and an after-end-of-fluorescence-occurrence period PFND corresponding to a predetermined period with the end of the fluorescence occurrence period PFP as a start point, during the after-end-of-fluorescence-occurrence period PFNB, to the image inputting portion 81 based on the video recording control information outputted from the video recording controlling portion 85. Further, the video recording managing portion 86 performs control for causing output of the white light images WIA to the image recording portion 83 to be stopped at an end of the after-end-of-fluorescence-occurrence period PFND, to the image inputting portion 81 based on the video recording control information outputted from the video recording controlling portion 85.

The video recording managing portion 86 performs control for setting an output destination of the fluorescence images FIA to the image recording portion 83, to the image inputting portion 81 based on the video recording control information outputted from the video recording controlling portion 85. Further, the video recording managing portion 86 performs control for causing output of the fluorescence images FIA to the image recording portion 83 to be performed during the fluorescence occurrence period PFP, to the image inputting portion 81 based on the video recording control information outputted from the video recording controlling portion 85. Further, the video recording managing portion 86 performs control for causing output of the fluorescence images FIA to the image recording portion 83 to be stopped during the fluorescence non-occurrence period PFN, to the image inputting portion 81 based on the video recording control information outputted from the video recording controlling portion 85.

Figure 5:
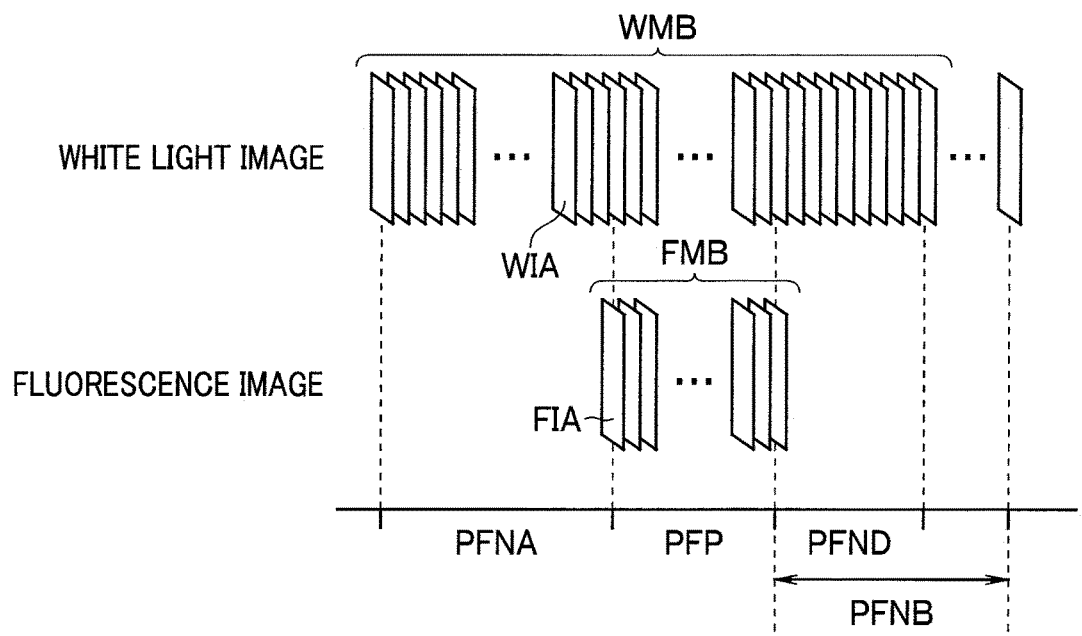
FIG. 5 is a diagram for illustrating an example of the recording state of images in the video recording apparatus according to the embodiment.

According to the operation as described above, when the video recording mode of the video recording apparatus 6 is set to the video recording mode RMB, a movie WMB corresponding to a plurality of white light images WIA sequentially inputted to the image inputting portion 81 during the before-start-of-fluorescence-occurrence period PFNA, the fluorescence occurrence period PFP and the after-end-of-fluorescence-occurrence period PFND is recorded to the image recording portion 83, for example, as shown in FIG. 5. Further, according to the operation as described above, when the video recording mode of the video recording apparatus 6 is set to the video recording mode RMB, a movie FMB corresponding to a plurality of fluorescence images FIA sequentially inputted to the image inputting portion 81 in the fluorescence occurrence period PFP is recorded to the image recording portion 83, for example, as shown in FIG. 5. FIG. 5 is a diagram for illustrating an example of the recording state of images in the video recording apparatus according to the embodiment.

In other words, when the video recording mode of the video recording apparatus 6 is set to the video recording mode RMB, the white light images WIA sequentially inputted to the video recording apparatus 6 during the before-start-of-fluorescence-occurrence period PFNA, the fluorescence occurrence period PFP and the after-end-of-fluorescence-occurrence period PFND are recorded as the movie WMB, and the fluorescence images FIA inputted to the video recording apparatus 6 during the fluorescence occurrence period PFP are recorded as the movie FMB. Further, when the video recording mode of the video recording apparatus 6 is set to the video recording mode RMB, control for causing the white light images WIA to be recorded to the image recording portion 83 is performed by the video recording managing portion 86 during the before-start-of-fluorescence-occurrence period PFNA, the fluorescence occurrence period PFP and the after-end-of-fluorescence-occurrence period PFND. Further, when the video recording mode of the video recording apparatus 6 is set to the video recording mode RMB, control for causing the fluorescence images FIA not to be recorded to the image recording portion 83 is performed by the video recording managing portion 86 during the fluorescence non-occurrence period PFN. Further, when the video recording mode of the video recording apparatus 6 is set to the video recording mode RMB, control for causing the fluorescence images FIA to be recorded to the image recording portion 83 is performed by the video recording managing portion 86 during the fluorescence occurrence period PFP.

For example, by operating the video recording mode setting switch of the input I/F 84, the user gives an instruction for setting a video recording mode RMC, a video recording mode in which white light images WIA sequentially outputted from the processor 4 in the fluorescence observation mode to be recorded to the video recording apparatus 6 only within a predetermined period.

The video recording controlling portion 85 generates video recording control information for causing recording of the white light images WIA to be performed from a time point before a predetermined period before the start of the fluorescence occurrence period PFP to a time point after a predetermined period after the end of the fluorescence occurrence period PFP, and outputs the video recording control information to the video recording managing portion 86, based on the analysis result information outputted from the image analyzing portion 46, the observation mode information outputted from the controlling portion 49 and the instructions of the recorded image setting switch and the video recording mode setting switch of the input I/F 84. Further, the video recording controlling portion 85 generates video recording control information for, while causing fluorescence images FIA to be recorded to the image recording portion 83 during the fluorescence occurrence period PFP, causing the fluorescence images FIA not to be recorded to the image recording portion 83 during the fluorescence non-occurrence period PFN, and outputs the video recording control information to the video recording managing portion 86, based on the analysis result information outputted from the image analyzing portion 46, the observation mode information outputted from the controlling portion 49 and the instruction from the recorded image setting switch of the input I/F 84.

The video recording managing portion 86 performs control for setting an output destination of the white light images WIA to the image holding portion 82 during the before-start-of-fluorescence-occurrence period PFNA, to the image inputting portion 81 based on the video recording control information outputted from the video recording controlling portion 85. In other words, the video recording managing portion 86 performs control for causing a predetermined number of white light images WIA to be held in the image holding portion 82 during the before-start-of-fluorescence-occurrence period PFNA, based on the video recording control information outputted from the video recording controlling portion 85. Then, in response to such control of the video recording managing portion 86, N (1≤N) white light images WIA including the newest white light image WIA acquired during the before-start-of-fluorescence-occurrence period PFNA are held in the image holding portion 82.

When detecting that the before-start-of-fluorescence-occurrence period PFNA transitions to the fluorescence occurrence period PFP, the video recording managing portion 86 performs control for causing the currently held N white light images WIA to be outputted to the image recording portion 83, to the image holding portion 82, and performs control for re-setting an output destination of the white light images WIA to the image recording portion 83, to the image inputting portion 81, based on the video recording control information outputted from the video recording controlling portion 85. In other words, at the start of the fluorescence occurrence period PFP, the video recording managing portion 86 performs control for causing output of the white light images WIA from the image inputting portion 81 to the image holding portion 82 to be stopped, control for causing the N white light images WIA held in the image holding portion 82 to be outputted to the image recording portion 83, and control for causing recording of the white light images WIA sequentially outputted from the white light image generating portion 43 via the image inputting portion 81 to the image recording portion 83 to be started, based on the video recording control information outputted from the video recording controlling portion 85. Further, the video recording managing portion 86 performs control for causing output of the white light images WIA to the image recording portion 83 to be performed during the fluorescence occurrence period PFP and the after-end-of-fluorescence-occurrence period PFND, to the image inputting portion 81 based on the video recording control information outputted from the video recording controlling portion 85. Further, the video recording managing portion 86 performs control for causing output of the white light images WIA to the image recording portion 83 to be stopped at the end of the after-end-of-fluorescence-occurrence period PFND, to the image inputting portion 81 based on the video recording control information outputted from the video recording controlling portion 85.

The video recording managing portion 86 performs control for setting an output destination of the fluorescence images FIA to the image recording portion 83, to the image inputting portion 81, based on the video recording control information outputted from the video recording controlling portion 85. Further, the video recording managing portion 86 performs control for causing output of the fluorescence images FIA to the image recording portion 83 to be performed during the fluorescence occurrence period PFP, to the image inputting portion 81 based on the video recording control information outputted from the video recording controlling portion 85. Further, the video recording managing portion 86 performs control for causing output of the fluorescence images FIA to the image recording portion 83 to be stopped during the fluorescence non-occurrence period PFN, to the image inputting portion 81 based on the video recording control information outputted from the video recording controlling portion 85.

Figure 6:
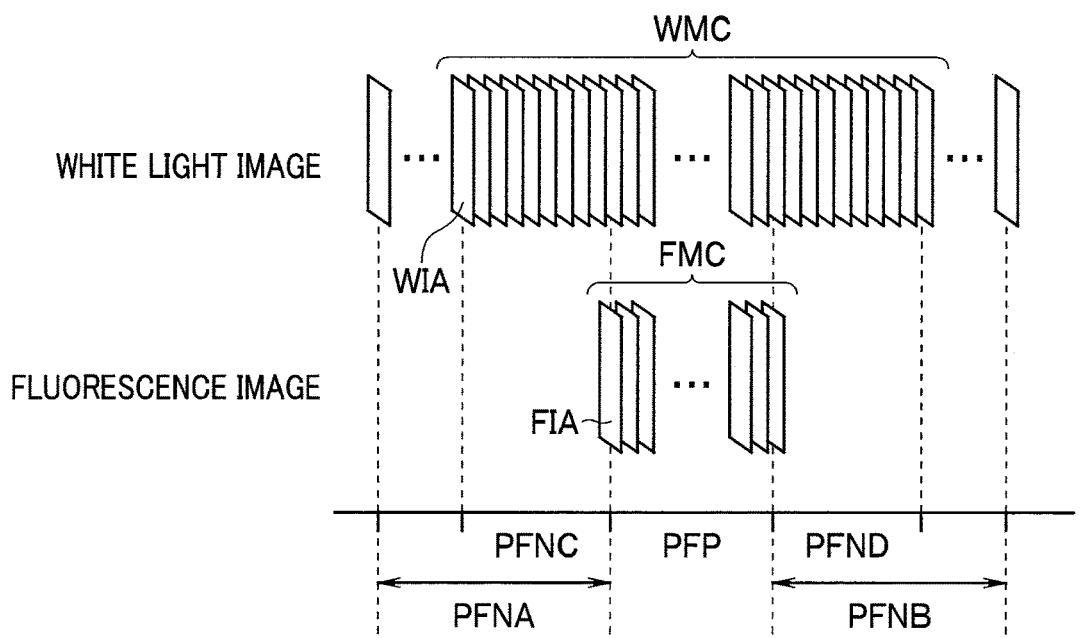
FIG. 6 is a diagram for illustrating an example of the recording state of images in the video recording apparatus according to the embodiment.

According to the operation as described above, when the video recording mode of the video recording apparatus 6 is set to the video recording mode RMC, a movie WMC corresponding to a plurality of white light images WIA sequentially inputted to the image inputting portion 81 during a before-start-of-fluorescence-occurrence period PFNC corresponding to a predetermined period required to acquire N white light images WIA during the before-start-of-fluorescence-occurrence period PFNA, the fluorescence occurrence period PFP and the after-end-of-fluorescence-occurrence period PFND is recorded to the image recording portion 83, for example, as shown in FIG. 6. Further, according to the operation as described above, when the video recording mode of the video recording apparatus 6 is set to the video recording mode RMC, a movie FMC corresponding to a plurality of fluorescence images FIA sequentially inputted to the image inputting portion 81 in the fluorescence occurrence period PFP is recorded to the image recording portion 83, for example, as shown in FIG. 6. FIG. 6 is a diagram for illustrating an example of the recording state of images in the video recording apparatus according to the embodiment.

In other words, when the video recording mode of the video recording apparatus 6 is set to the video recording mode RMC, the white light images WIA sequentially inputted to the video recording apparatus 6 during the before-start-of-fluorescence-occurrence period PFNC, the fluorescence occurrence period PFP and the after-end-of-fluorescence-occurrence period PFND are recorded as the movie WMC, and the fluorescence images FIA inputted to the video recording apparatus 6 during the fluorescence occurrence period PFP are recorded as the movie FMC. Further, when the video recording mode of the video recording apparatus 6 is set to the video recording mode RMC, control for causing the white light images WIA to be recorded to the image recording portion 83 is performed by the video recording managing portion 86 during the before-start-of-fluorescence-occurrence period PFNC, the fluorescence occurrence period PFP and the after-end-of-fluorescence-occurrence period PFND. Further, when the video recording mode of the video recording apparatus 6 is set to the video recording mode RMC, control for causing the fluorescence images FIA not to be recorded to the image recording portion 83 is performed by the video recording managing portion 86 during the fluorescence non-occurrence period PFN. Further, when the video recording mode of the video recording apparatus 6 is set to the video recording mode RMC, control for causing the fluorescence images FIA to be recorded to the image recording portion 83 is performed by the video recording managing portion 86 during the fluorescence occurrence period PFP.

As described above, the video recording managing portion 86 estimates a period during which an analysis result that a fluorescence occurrence area is not included is obtained by the process of the image analyzing portion 46, as the fluorescence non-occurrence period PFN to perform control, based on the video recording control information outputted from the video recording controlling portion 85. Further, the video recording managing portion 86 estimates a period during which an analysis result that a fluorescence occurrence area is included is obtained by the process of the image analyzing portion 46, as the fluorescence occurrence period PFP to perform control, based on the video recording control information outputted from the video recording controlling portion 85. Further, as described above, the video recording managing portion 86 performs control for causing the white light images WIA and the fluorescence images FIA to be recorded to the image recording portion 83, during the fluorescence occurrence period PFP. Further, as described above, when the video recording mode of the video recording apparatus 6 is set to the video recording mode RMC, the video recording managing portion 86 performs control for causing the white light images WIA corresponding to the predetermined period before the start of the fluorescence occurrence period PFP during the fluorescence non-occurrence period PFN to be recorded to the image recording portion 83.

In the present embodiment, for example, the image recording portion 83 may be such that, in response to control of the video recording managing portion 86, performs an operation for setting an image quality (a resolution) of white light images WIA inputted to the image inputting portion 81 during the fluorescence non-occurrence period PFN to a relatively low image quality (a low resolution) to record the white light images WIA and performs an operation for setting an image quality (a resolution) of white light images WIA inputted to the image inputting portion 81 during the fluorescence occurrence period PFP to a relatively high quality (a high resolution) to record the white light images WIA.

As described above, according to the present embodiment, fluorescence images FIA acquired during a period during which fluorescence FLA is invisible and a period during which visibility of the fluorescence FLA is low are not video-recorded, and fluorescence images FIA acquired during a period during which the visibility of the fluorescence FLA is high are video-recorded. Therefore, according to the present embodiment, it is possible to acquire, for example, video-recorded data with a minimized data size so that only fluorescence images FIA thought to be required for work such as diagnosis are included, and, as a result, it is possible to efficiently video-record the fluorescence images FIA acquired in the fluorescence observation mode.

Further, as described above, according to the present embodiment, when the video recording mode of the video recording apparatus 6 is set to the video recording mode RMB, white light images WIA (superposed images SIA) acquired during a period from a time point before a state in which fluorescence FLA is visible starts to a time point immediately after a state in which fluorescence FLA is completely invisible starts are video-recorded, and white light images WIA (superposed images SIA) acquired after the period are not video-recorded. Therefore, according to the present embodiment, when the video recording mode of the video recording apparatus 6 is set to the video recording mode RMB, it is possible to acquire, for example, video-recorded data with a compact data size so that white light images WIA (superposed images SIA) thought to be required for work such as diagnosis are included, and, as a result, it is possible to efficiently video-record white light images WIA (superposed images SIA) acquired in the fluorescence observation mode.

Further, as described above, according to the present embodiment, when the video recording mode of the video recording apparatus 6 is set to the video recording mode RMC, white light images WIA (superposed images SIA) acquired during a period from a time point immediately before the state in which fluorescence FLA is visible starts to a time point immediately after the state in which fluorescence FLA is completely invisible starts are video-recorded, and white light images WIA (superposed images SIA) acquired outside the period are not video-recorded. Therefore, according to the present embodiment, when the video recording mode of the video recording apparatus 6 is set to the video recording mode RMC, it is possible to acquire, for example, video-recorded data with a minimized data size so that only white light images WIA (superposed images SIA) thought to be required for work such as diagnosis, and, as a result, it is possible to efficiently video-record white light images WIA (superposed images SIA) acquired in the fluorescence observation mode.

Note that, according to the present embodiment, for example, the image analyzing portion 46 may perform a process for, based on a feature value related to a color tone of superposed images SIA outputted from the superposed image generating portion 45, analyzing whether an fluorescence occurrence area is included in the superposed images SIA or not, in the fluorescence observation mode, and output analysis result information showing an analysis result obtained by the process to the video recording apparatus 6.

Further, according to the present embodiment, for example, the image analyzing portion 46 may perform a process for comparing a white light image WIA outputted from the white light image generating portion 43 and a superposed image SIA outputted from the superposed image generating portion 45 and output analysis result information showing an obtained analysis result to the video recording apparatus 6, in the fluorescence observation mode.

For example, if analysis result information showing an analysis result that the white light image WIA outputted from the white light image generating portion 43 corresponds to the superposed image SIA outputted from the superposed image generating portion 45 is outputted from the image analyzing portion 46, an operation that is substantially the same as the operation in the case where an analysis result showing that an fluorescence occurrence area is not included in a fluorescence image FIA outputted from the fluorescence image generating portion 44 is obtained is performed in the video recording apparatus 6. Further, for example, if analysis result information showing an analysis result that the white light image WIA outputted from the white light image generating portion 43 does not correspond to the superposed image SIA outputted from the superposed image generating portion 45 is outputted from the image analyzing portion 46, an operation that is substantially the same as the operation in the case where an analysis result showing that an fluorescence occurrence area is included in fluorescence images FIA outputted from the fluorescence image generating portion 44 is obtained is performed in the video recording apparatus 6.

Further, according to the present embodiment, for example, the image analyzing portion 46 may be configured having a function as a distance calculating portion configured to perform a process for calculating an observation distance VD corresponding to a distance between the distal end portion of the insertion portion 21 of the endoscope 2 and an object to which the excitation light EXA is radiated, based on white light images WIA outputted from the white light image generating portion 43, in the fluorescence observation mode. In such a case, for example, the image analyzing portion 46 can output analysis result information showing an analysis result obtained by comparing the observation distance VD and a predetermined value THW, to the video recording apparatus 6. Further, in the case as described above, for example, the video recording managing portion 86 can estimate a period during which an analysis result that the observation distance VD is equal to or above a predetermined threshold THW as the fluorescence non-occurrence period PFN to perform control and estimate a period during which an analysis result that the observation distance VD is below the predetermined threshold THW as the fluorescence occurrence period PFP to perform control, based on the video recording control information outputted from the video recording controlling portion 85.

According to the present embodiment, for example, when an instruction for causing predetermined additional information to be recorded together at the time of video recording is given on the input I/F 84, video recording control information corresponding to the instruction may be outputted from the video recording controlling portion 85, and control corresponding to the video recording control information may be performed by the video recording managing portion

86. A specific example of an operation performed in such a case will be described below.

Figure 7:
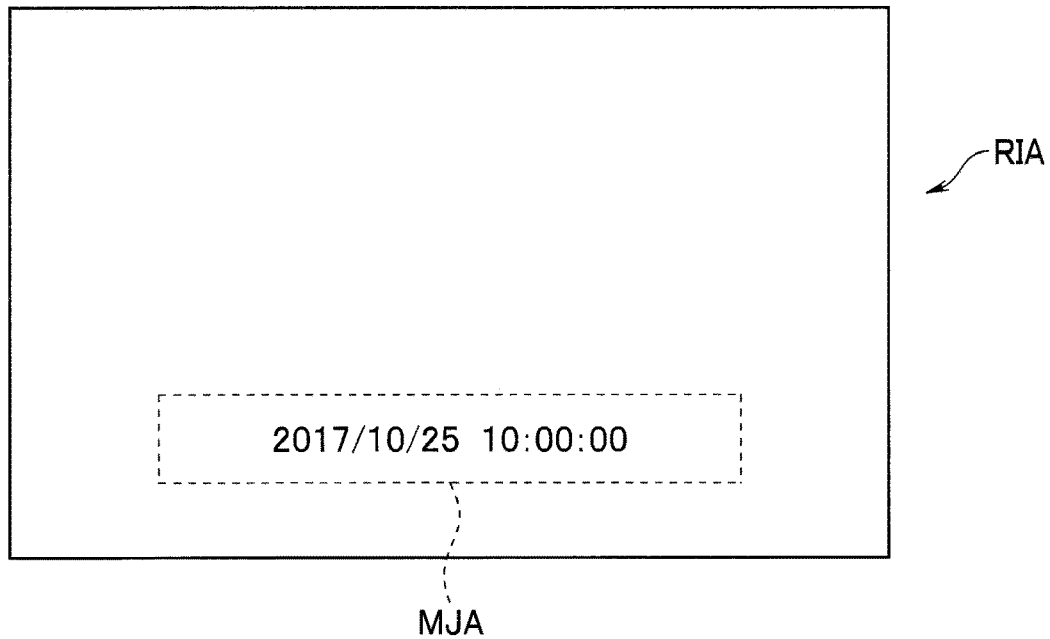
FIG. 7 is a diagram for illustrating an example of additional information recorded to the video recording apparatus according to the embodiment.

For example, when an instruction for causing a time stamp to be recorded together at the time of video recording is given on the input I/F 84, the video recording managing portion 86 may perform control for causing character information showing a date and time when a recording target image RIA (corresponding to at least one image among the white light images WIA, the fluorescence images FIA and the superposed images SIA), which is an image set as a recording target, was inputted to be added to the recording target image RIA to perform recording, to the image recording portion 83, according to the video recording control information outputted from the video recording controlling portion 85. According to such control of the video recording managing portion 86, an operation for adding character information MJA showing the date and time when the recording target image RIA was inputted, at a lower part of the recording target RIA to perform recording is performed by the image recording portion 83 (see FIG. 7). FIG. 7 is a diagram for illustrating an example of additional information recorded to the video recording apparatus according to the embodiment.

Figure 8:
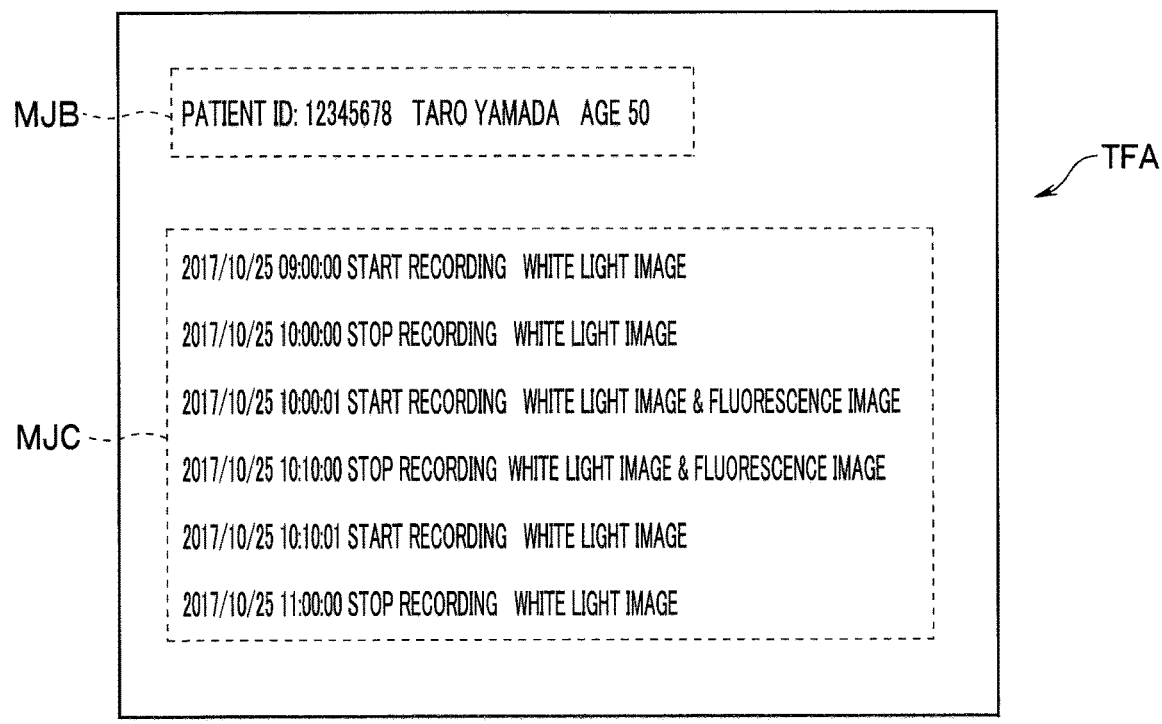
FIG. 8 is a diagram for illustrating an example of the additional information recorded to the video recording apparatus according to the embodiment.

For example, when an instruction for causing metadata to be recorded together at the time of video recording is given on the input I/F 84, the video recording managing portion 86 may perform control for causing character information including a recording start date and time and a recording end time and date of the recording target image RIA to be recorded separately from the recording target image RIA, to the image recording portion 83, according to the video recording control information outputted from the video recording controlling portion 85. According to such control of the video recording managing portion 86, for example, an operation for generating and recording a text file TFA, which has pieces of character information MJB and MJC as shown in FIG. 8 and is data separate from the recording target image RIA is performed by the image recording portion 83. FIG. 8 is a diagram for illustrating an example of the additional information recorded to the video recording apparatus according to the embodiment.

The character information MJB in FIG. 8 includes, for example, information about a patient inputted by the user operating the input I/F 84 before performing observation by the endoscope 2. Further, the character information MJC in FIG. 8 includes, for example, a recording start time and date and a recording end time and date in a case where recording target images in the white observation mode is set to white light images WIA, and a recording start time and date and a recording end time and date in a case where recording target images in the fluorescence observation mode are set to white light images WIA and fluorescence images FIA. Note that when the video recording mode RMA described above is given as an example, "2017/10/25 09:00:00" included in the character information MJC in FIG. 8 corresponds to the recording start time and date of white light images WIA; "2017/10/25 11:00:00" included in the character information MJC corresponds to the recording end time and date of the white light images WIA; "2017/10/25 10:00:01" included in the character information MJC corresponds to the recording start time and date of white light images WIA and fluorescence images FIA; and "2017/10/25 10:10:00" included in the character information MJC corresponds to the recording end time and date of the white light images WIA and the fluorescence images FIA. Further, when the video recording mode RMA described above is given as an example, "2017/10/25 10:00:00" included in the character information MJC in FIG. 8 corresponds to a time and date of an end of the before-start-of-fluorescence-occurrence period PFNA, and "2017/10/25 10:10:01" included in the character information MJC corresponds to a time and date of a start of the after-end-of-fluorescence-occurrence period PFNB.

Figure 9:
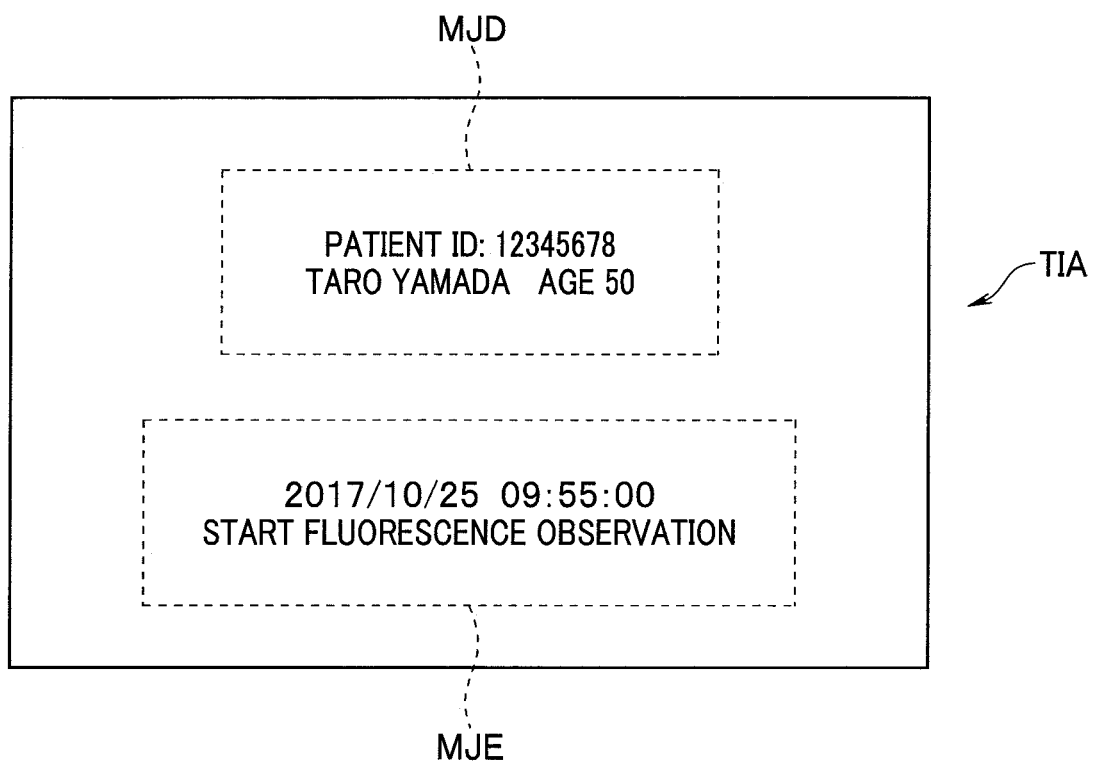
FIG. 9 is a diagram for illustrating an example of the additional information recorded to the video recording apparatus according to the embodiment.

For example, when an instruction for causing title information to be recorded together at the time of video recording is given on the input OF 84, the video recording managing portion 86 may perform control for causing a title image, which is an image including character information for informing that the fluorescence occurrence period PFP has been started, to be recorded as additional information and causing fluorescence images FIA to be recorded immediately after the title image, to the image recording portion 83, according to video recording control information outputted from the video recording controlling portion 85. According to such control of the video recording managing portion 86, for example, an operation for generating one or more title images TIA including the pieces of character information MJD and MJE as shown in FIG. 9 and starting recording of fluorescence images FIA after inserting the generated title images TIA into a forefront part of the movie FMA, FMB or FMC described above is performed by the image recording portion 83. FIG. 9 is a diagram for illustrating an example of the additional information recorded to the video recording apparatus according to the embodiment.

The character information MJD in FIG. 9 includes, for example, information about the patient inputted by the user operating the input I/F 84 before performing observation by the endoscope 2. Further, character information MJE in FIG. 9 includes, for example, information showing a time and date of the start of the fluorescence occurrence period PFP.

In the present embodiment, instead of the operation of inserting the title images TIA described above, for example, such an operation of superposing visual information such as an icon capable of informing that the fluorescence occurrence period PFP has been started on one or more fluorescence images FIA belonging to the forefront part of the movie FMA, FMB or FMC may be performed by the image recording portion 83.

The present invention is not limited to the embodiment described above, but various changes and applications are, of course, possible within a range not departing from the spirit of the invention.

What is claimed is:
1. An endoscope system comprising:
   a processor;
   a light source configured to be capable of emitting excitation light for causing a fluorescent agent administered to a subject to be excited and illumination light for illuminating an inside of the subject; and
   an image pickup device configured to pick up images of each of fluorescence that occurs in response to radiation of the excitation light to an object existing inside the subject to whom the fluorescent agent has been administered, and reflected light that occurs in response to radiation of the illumination light to the object; wherein
   the processor generates and sequentially outputs reflected light images which are images corresponding to the reflected light picked up by the image pickup device;
   generates and sequentially outputs fluorescence images which are images corresponding to the fluorescence light picked up by the image pickup device;
   records each of the sequentially outputted reflected light images and the sequentially outputted fluorescence images to a first storage medium;

performs control for causing the reflected light images and the fluorescence images to be recorded to the first storage medium in a fluorescence occurrence period, which is a period during which the fluorescence occurs, performs control for causing the fluorescence images not to be recorded to the first storage medium during a fluorescence non-occurrence period, which is a period during which the fluorescence does not occur, and performs control for causing reflected light images corresponding to a predetermined period before start of the fluorescence occurrence period during the fluorescence non-occurrence period, among the reflected light images, to be recorded to the first storage medium; and furthermore, performs control for causing the reflected light images to be recorded to the first storage medium during an after-end-of-fluorescence-occurrence period corresponding to a predetermined period with an end of the fluorescence occurrence period as a start point, and performs control for causing the reflected light images not to be recorded to the first storage medium during the fluorescence non-occurrence period after an end of the after-end-of-fluorescence-occurrence period.

2. An endoscope system comprising:
a processor;
a light source configured to be capable of emitting excitation light for causing a fluorescent agent administered to a subject to be excited and illumination light for illuminating an inside of the subject; and
an image pickup device configured to pick up images of each of fluorescence that occurs in response to radiation of the excitation light to an object existing inside the subject to whom the fluorescent agent has been administered, and reflected light that occurs in response to radiation of the illumination light to the object; wherein
the processor generates and sequentially outputs reflected light images which are images corresponding to the reflected light picked up by the image pickup device;
generates and sequentially outputs fluorescence images which are images corresponding to the fluorescence light picked up by the image pickup device;
records each of the sequentially outputted reflected light images and the sequentially outputted fluorescence images to a first storage medium;
performs control for causing the reflected light images and the fluorescence images to be recorded to the first storage medium in a fluorescence occurrence period, which is a period during which the fluorescence occurs, performs control for causing the fluorescence images not to be recorded to the first storage medium in a fluorescence non-occurrence period, which is a period during which the fluorescence does not occur, and performs control for causing the reflected light images corresponding to a predetermined period before start of the fluorescence occurrence period during the fluorescence non-occurrence period, among the reflected light images, to be recorded to the first storage medium;
furthermore, holds a predetermined number of the sequentially outputted reflected light images in a second storage medium; and
performs control for causing the predetermined number of the reflected light images to be held in the second storage medium during a before-start-of-fluorescence-occurrence period corresponding to a period before start of occurrence of the fluorescence during the fluorescence non-occurrence period, and performs control for causing output of the reflected light images to the second storage medium to be stopped, control for causing the predetermined number of the reflected light images held in the second storage medium to be outputted to the first storage medium and control for causing recording of the sequentially outputted reflected light images to the first storage medium to be started, at the start of the fluorescence occurrence period.

3. The endoscope system according to claim 1, wherein the processor performs a process for analyzing whether a fluorescence occurrence area is included in the fluorescence images, based on a feature value related to brightness of the fluorescence images; and
estimates a period during which an analysis result that the fluorescence occurrence area is not included, as the fluorescence non-occurrence period, to perform control, and estimates a period during which an analysis result that the fluorescence occurrence area is included, as the fluorescence occurrence period, to perform control.

4. The endoscope system according to claim 1, wherein the processor performs a process for calculating an observation distance corresponding to a distance between a distal end portion of an insertion portion of an endoscope provided with the image pickup device and the object to which the excitation light is radiated, based on the reflected light images; and
estimates a period during which an analysis result that the observation distance is equal to or above a predetermined threshold, as the fluorescence non-occurrence period, to perform control, and estimates a period during which an analysis result that the observation distance is below the predetermined threshold, as the fluorescence occurrence period, to perform control.

5. The endoscope system according to claim 1, wherein the processor generates and sequentially outputs superposed images obtained by superposing the reflected light images and the fluorescence images, respectively; and
performs control for causing the superposed images to be recorded to the first storage medium instead of the reflected light images and performs control for causing superposed images corresponding to the predetermined period, among the superposed images, to be recorded to the first storage medium instead of the reflected light images, during the fluorescence occurrence period.

6. The endoscope system according to claim 1, wherein the processor also performs, at time of performing control for causing a recording target image corresponding to at least any one of the reflected light images and the fluorescence images to be recorded to the first storage medium, control for adding information showing a time and date when the recording target image is inputted to the first storage medium to the recording target image to cause the recording target image to be recorded.

7. The endoscope system according to claim 1, wherein the processor also performs, at time of performing control for causing a recording target image corresponding to at least any one of the reflected light images and the fluorescence images to be recorded to the first storage medium, control for causing information including a recording start time and date and a recording end time and date of the recording target image to be recorded separately from the recording target image.

8. The endoscope system according to claim 1, wherein the processor performs control for causing a title image including information for informing that the fluorescence occurrence period has been started to be recorded and causing the fluorescence images to be recorded immediately after the title image.

9. An endoscope processor comprising a processor configured to process a signal about fluorescence generated by causing a fluorescent agent administered to a subject to be excited and a signal about reflected light that occurs in response to illumination to an inside of the subject; wherein
the processor generates reflected light images from the signal about the reflected light and sequentially outputs the reflected light images;
generates fluorescence images from the signal about the fluorescence and sequentially outputs the fluorescence light images;
performs control for causing the reflected light images and the fluorescence images to be recorded to an external recording apparatus in a fluorescence occurrence period, which is a period during which the fluorescence occurs, performs control for causing the fluorescence images not to be recorded to the external recording apparatus in a fluorescence non-occurrence period, which is a period during which the fluorescence does not occur, and performs control for causing reflected light images corresponding to a predetermined period before start of the fluorescence occurrence period during the fluorescence non-occurrence period, among the reflected light images, to be recorded to the external recording apparatus; and
furthermore, performs control for causing the reflected light images to be recorded to the external recording apparatus during an after-end-of-fluorescence-occurrence period corresponding to a predetermined period with an end of the fluorescence occurrence period as a start point, and performs control for causing the reflected light images not to be recorded to the external recording apparatus during the fluorescence non-occurrence period after an end of the after-end-of-fluorescence-occurrence period.

* * * * *